(12) United States Patent
Laue et al.

(10) Patent No.: US 7,342,654 B2
(45) Date of Patent: Mar. 11, 2008

(54) DETECTION OF IMPURITIES IN CYLINDRICALLY SHAPED TRANSPARENT MEDIA

(75) Inventors: Christian Laue, Mainz (DE); Gernot Brasen, Mainz (DE); Frank Lautenbach, Mainz (DE); Matthias Loeffler, Eisenberg (DE); Heiko Theuer, Mainz (DE)

(73) Assignee: International Business Machines Corporation, Armonk, NY (US)

( * ) Notice: Subject to any disclaimer, the term of this patent is extended or adjusted under 35 U.S.C. 154(b) by 411 days.

(21) Appl. No.: 10/904,986

(22) Filed: Dec. 8, 2004

(65) Prior Publication Data

US 2005/0134843 A1    Jun. 23, 2005

(30) Foreign Application Priority Data

Dec. 19, 2003    (EP) ................................. 03104833

(51) Int. Cl.
 *G01N 21/00* (2006.01)
(52) U.S. Cl. ................. 356/239.1; 356/237.1; 356/239.4
(58) Field of Classification Search ............ 356/239.1, 356/239.4, 240.1
See application file for complete search history.

(56) References Cited

U.S. PATENT DOCUMENTS

| | | | |
|---|---|---|---|
| 3,565,536 A * | 2/1971 | Wuellner et al. ......... | 356/239.1 |
| 4,500,203 A * | 2/1985 | Bieringer .................. | 356/239.4 |
| 4,547,067 A * | 10/1985 | Watanabe ................. | 356/239.1 |
| 4,655,349 A * | 4/1987 | Joseph et al. ............. | 209/524 |
| 4,691,231 A * | 9/1987 | Fitzmorris et al. ........ | 348/127 |
| 4,914,309 A * | 4/1990 | Masaharu et al. ......... | 250/559.48 |
| 4,948,956 A * | 8/1990 | Fukuchi ................... | 250/223 B |
| 5,969,810 A * | 10/1999 | Nicks et al. ............. | 356/239.4 |
| 6,067,155 A * | 5/2000 | Ringlien .................. | 356/240.1 |
| 6,104,482 A * | 8/2000 | Brower et al. ........... | 356/239.4 |
| 7,148,961 B1 * | 12/2006 | Ringlien .................. | 356/240.1 |

* cited by examiner

*Primary Examiner*—Gregory J. Toatley, Jr.
*Assistant Examiner*—Jarreas Underwood
(74) *Attorney, Agent, or Firm*—Todd M. C. Li

(57) ABSTRACT

The invention relates to a system and method of detecting impurities in a cylindrically shaped transparent medium, wherein the cylindrically shaped transparent medium is illuminated with electromagnetic radiation, and the radiation having components emerging radially from the medium, and at least some of the components are received by a detector for detecting impurities of the medium. The components are detected at a multiplicity of relative angular positions around the symmetry axis of the cylinder, so as to form an impurity diagram that may be analyzed to detect and measure impurities in the medium.

18 Claims, 6 Drawing Sheets

DETECTION OF IMPURITIES IN CYLINDRICALLY SHAPED TRANSPARENT MEDIA

BACKGROUND OF THE INVENTION

The present invention relates to the field of detecting and measuring impurities in cylindrically shaped transparent media.

Glass rods with a circular cross section are manufactured on a large scale as preliminary product for e.g. semiconductor or chemical industry. Glass rods are typically produced from a cast by means of an elongation process. However the quality of the produced glass rods strongly depends on the number of contaminants or impurities that are embedded in the glass. In typical production processes of glass rods, the majority of impurities or contaminants consists of gas bubbles embedded in the bulk of the material.

In order to guarantee a quality standard of the glass product, its purity has to be monitored continuously, i.e. the number of gas bubbles embedded in the glass rod per unit volume has to be measured. Determining the purity of a glass rod allows to sort it into different quality categories. Furthermore the permanent or frequent inspection of the glass rod during production allows corrective action to be taken in order to maintain a required quality or purity standard.

The inspection of glass or media that are transparent for a specific wavelength of electromagnetic radiation is known in the prior art by making use of imaging techniques by means of cameras or photo detectors. Such optical inspection methods are mostly limited to surface inspections, hence the detection of surface defects. Volume defects such as particles or gas bubbles embedded in the bulk of a transparent medium can only be inspected and detected when the medium is sufficiently thin or features a plain surface. Optical inspection means that are known in the prior art do not provide detection and measuring of impurities located in the bulk of a medium having a curved surface. Furthermore the optical inspection of a medium featuring a non-planar surface is problematic due to refraction and reflection at the boundary of the medium. In particular, refraction and internal reflections that may occur for specific angles of incidence of the electromagnetic radiation, do not allow a sufficient inspection of the entire bulk medium.

Therefore, there is a need to provide a method and system for detecting impurities in a cylindrically shaped medium that allows inspection of the entire bulk medium.

SUMMARY OF THE INVENTION

It is an objection of the present invention to provide a detection method, a detection system and a computer program product for detection and measuring of impurities of a cylindrically shaped medium.

It is a further objective of the present invention to provide a method and system for inspecting the entire bulk medium of a cylindrically shaped medium for impurities.

It is a further objective to provide a method and system for determining characteristics of impurities within a cylindrically shaped bulk medium, including, but not limited to, the longitudinal position, the radial position, the circumferential position, the angular width and the vertical dimension of the impurities.

The invention provides a method of detecting impurities in a cylindrically shaped transparent medium. The impurities are detected optically by illuminating the cylindrically shaped medium by electromagnetic radiation and detecting radiation emerging from the medium. The invention uses a detector to detect preferably the radial components of the radiation emerging perpendicular to the surface of the cylindrically shaped medium.

According to one aspect of the present invention, a method of detecting impurities in a cylindrically shaped transparent medium is provided, the method including the steps of:

illuminating the cylindrically shaped transparent medium with electromagnetic radiation, the radiation having radiation components emerging radially from the medium; and receiving at least some of the radiation components by a detector for detecting impurities of the medium.

In another aspect, the present invention further comprises the steps of:

storing a plurality of spatial patterns of the radiation components for a plurality of relative angular positions between the detector and the cylindrically shaped medium, the spatial patterns being indicative of the impurities of the medium;

forming an impurity diagram comprising an arrangement of the spatial patterns arranged in accordance with the plurality of relative angular positions; and determining one or more characteristics of the impurities comprising an analysis of the impurity diagram. The characteristics of the impurities to be determined include, but are not limited to the size, longitudinal position, radial position, circumferential position or a combination thereof.

According to another aspect of the present invention, the quality and the accuracy of the spatial pattern of detected radiation (i.e. the signal-to-noise ratio) can be improved by detecting a first and a second radiation pattern at a first and a second relative angular position, the first and the second relative angular positions being shifted by 180 degrees.

According to yet another aspect of the present invention, a plurality of spatial patterns of the radiation components for a plurality of relative angular positions between the detector and the cylindrically shaped medium can be obtained by providing relative angular movement between the cylindrically shaped medium and one or more detectors around the longitudinal axis of the cylindrically shaped medium. A plurality of detectors and sources may also be used to provide a plurality of relative angular position, either alone, or in combination with relative angular movement of the medium and the detectors.

According to yet another aspect of the invention, the cylindrically shaped medium and the detector may move in a translational way relative to each other along the longitudinal direction of the cylindrically shaped medium with a longitudinal speed.

According to another aspect of the invention, a system is provided for detecting impurities in a cylindrically shaped medium, the system comprising:

a radiation source for illuminating the cylindrically shaped transparent medium with electromagnetic radiation; and a detector for receiving radial components of radiation that emerge radially from the medium.

The system according to the invention may further comprise:

Means for storing a plurality of spatial patterns of the radial components for a plurality of relative angular positions between the detector and the cylindrically shaped medium, the plurality of spatial patterns being indicative of the impurities of the medium; and Means for determining a characteristic of the impurities in accordance with the plurality of spatial patterns of radiation components.

Means for obtaining a plurality of relative angular positions may include a combination of relative angular movement of the cylindrically shaped medium and the detector around the longitudinal axis of the cylindrically shaped medium, a plurality of sources and a plurality of detectors.

According to another aspect of the invention, an impurity diagram is formed from an arrangement of the plurality of spatial patterns arranged in accordance with the plurality of relative angular positions.

According to yet another aspect of the invention, the system includes a detector having a first transverse expansion parallel to the longitudinal axis of the cylindrically shaped medium and a second transverse expansion perpendicular to the longitudinal axis of the cylindrically shaped medium, the first transverse expansion of the detector being larger than the second transverse expansion of the detector.

According to another aspect of the invention, the system may further comprise two or more sources of electromagnetic radiation generating an electromagnetic field distribution inside the cylindrically shaped medium, the electromagnetic field distribution covering a portion of the circular cross section of the cylindrically shaped medium.

According to another aspect of the present invention, the signal-to-noise ration of the spatial patterns is improved by providing at least first and second detectors arranged at a relative angular position of 180° from each other around the longitudinal axis of the cylindrically shaped medium.

In yet another aspect of the invention, the system further includes a means for forming an impurity diagram comprising an arrangement of the spatial patterns arranged in accordance with the plurality of relative angular positions; and a means for determining one or more characteristics of the impurities comprising an analysis of the impurity diagram. The characteristics of the impurities to be determined include, but are not limited to the size, longitudinal position, radial position, circumferential position or a combination thereof.

BRIEF DESCRIPTION OF THE DRAWINGS

In the following, preferred embodiments of the invention will be described in greater detail by making reference to the drawings, which are not necessarily drawn to scale, in which.

DETAILED DESCRIPTION

The invention provides a method of detecting impurities in a cylindrically shaped transparent medium. The impurities are detected optically by illuminating the cylindrically shaped medium by electromagnetic radiation and detecting radiation emerging from the medium.

Figure 1:
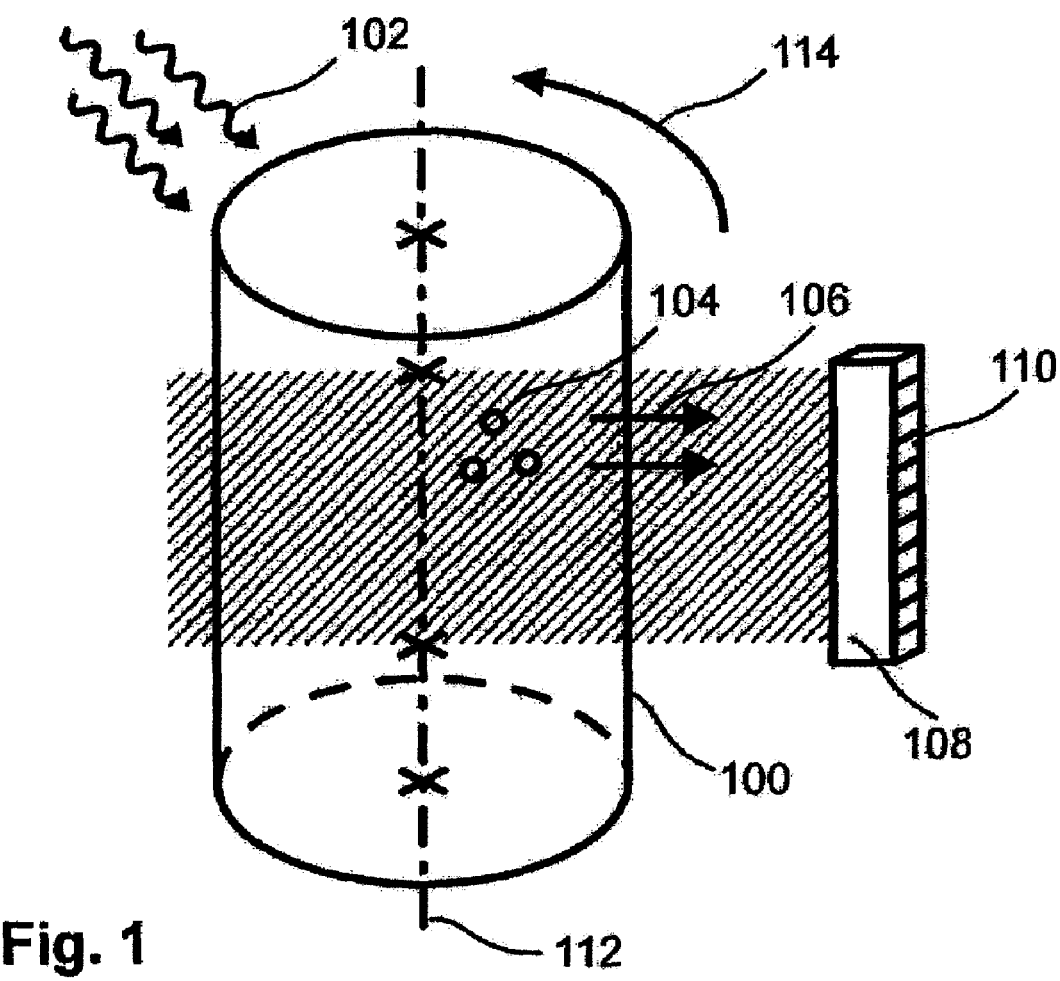
FIG. 1 shows a perspective view of the cylindrically shaped medium and the detector.

FIG. 1 shows a perspective view of the cylindrically shaped medium 100 being illuminated by electromagnetic radiation 102.

The radiation 102 interacts with impurities 104 in the bulk medium.

The invention uses a detector 108 to detect preferably the components 106 of the radiation propagating perpendicular to the cylindrical axis and thus emerging perpendicular to the surface of the cylindrically shaped medium. These components of the radiation propagate in a radial direction in the cylindrically shaped medium and will be referred to in this text as "radial components" 106 of the radiation or as radiation components in the diametral plane of the cylinder 100. These radial components 106 of the radiation are not refracted at the surface of the medium 100. The transmission without refraction allows for an undistorted imaging of the volume of the cylindrically shaped medium that has been traversed by the radial components of the electromagnetic radiation.

The radial component 106 of the radiation emerging from the medium 100 is detected by a detector 108. The detector 108 is sensitive to the electromagnetic radiation 102, 106 and comprises a number of detector pixels 110. For the detection of impurities in the bulk of the cylindrically shaped medium 100 only the radial components 106 of the electromagnetic radiation are relevant. Therefore, the transmission and detection of non-radial components of electromagnetic radiation may be suppressed by appropriate apertures (not shown). By using only the radial components 106 of the electromagnetic radiation emerging from the cylindrically shaped medium 100, the diametral plane across the cylindrical bulk material 100 is analyzed. The irradiated radiation interacts with impurities in the material and some of the radiation is reflected, scattered or diffracted at the impurities. The radial component 106 of this radiation is detected.

In accordance with the present invention, the method of detecting impurities can be applied to a plurality of different media. In principle the invention is applicable to a medium when it is transparent for a type of electromagnetic radiation that can be detected by the detector. For example when the cylindrically shaped medium 100 is a glass rod that is transparent for visible light, the wavelength of the electromagnetic radiation can be any wavelength of the visible wavelength region and must be detectable by the detector 108. In this case the detector 108 can be a commercially available charge coupled device (CCD) camera, a photo detector, or even any photo sensitive material as e.g. a photographic film. The method is not limited to such media that are transparent in the visible wavelength region. For example semi-conductor materials that are transparent in the infrared wavelength region can be subject to impurity inspection when the source of radiation and the type of detector are correspondingly chosen.

Furthermore the cylindrically shaped medium 100 and the detector 108 perform a relative and angular movement around the longitudinal axis (or rotation axis) 112 of the cylindrically shaped medium 100. A sense of rotation is indicated by the rotation direction 114, although the particular direction of relative rotation may be reversed. The relative angular movement can be realized either by rotating the cylindrically shaped medium 100 around the rotation axis 112 while keeping the detector 108 stationary, or by rotating the detector 108 around the rotation axis 112 and keeping the cylindrical shaped medium 100 stationary. The source of radiation 102 may also be rotated around the rotation axis 112. In all cases, the rotation axis 112 is identical with the symmetry axis of the cylindrically shaped medium 100, hence through the center of the circular cross section of the cylindrically shaped medium 100. In this way the detector receives radial components 106 of electromagnetic radiation from each circumferential position with respect to the cylindrically shaped medium 100, i.e. the entire circular cross section of the cylindrically shaped medium 100 is "scanned".

The relative angular movement can be realized by keeping the detector 108 and sources (e.g. 502, 504 of FIG. 5) of electromagnetic radiation stationary while rotating the cylindrically shaped medium 100 around its longitudinal axis 112. Alternatively the cylindrically shaped medium 100 can be kept stationary while the detector 108 and the source of electromagnetic radiation 102 rotate around the cylindrically shaped medium 100 with the longitudinal axis 112 of the cylindrically shaped medium as rotation axis 112. Moreover it is sufficient that only the detector 108 rotates around the cylindrically shaped medium 100 when radial components of radiation for all circumferential positions of the detector are present and can be detected.

Figure 2:
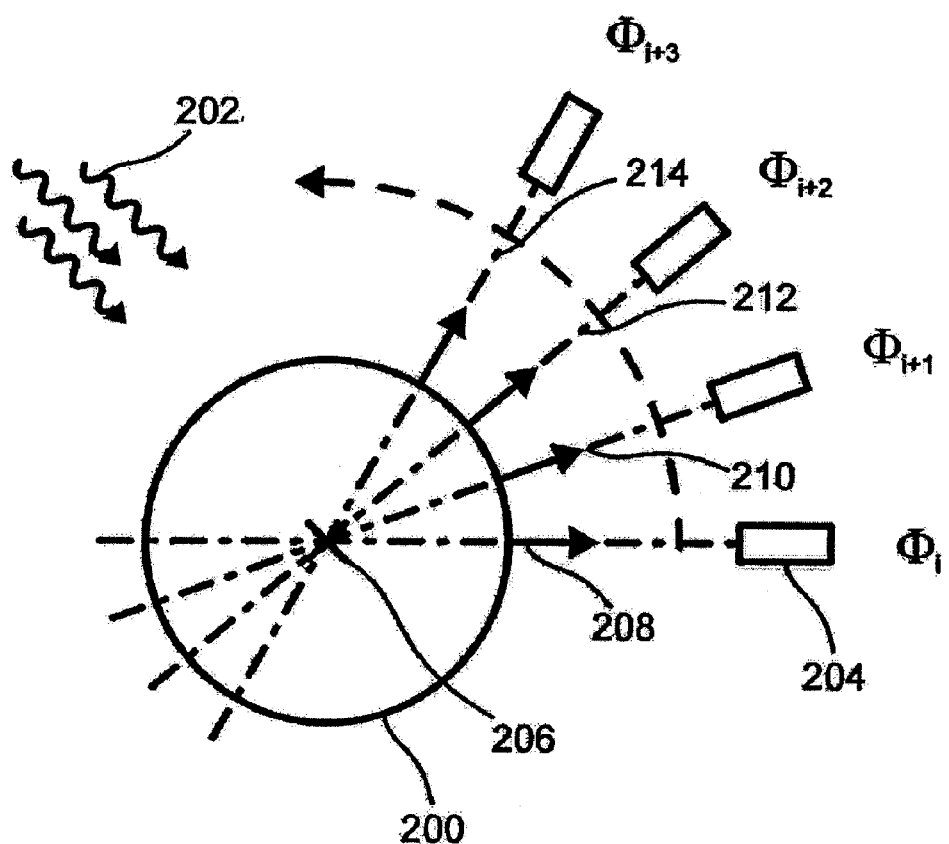
FIG. 2 shows a cross section of the cylindrically shaped medium and the detector.

Refer now to FIG. 2, which illustrates a cross sectional view of the cylindrically shaped medium 200 illuminated by electromagnetic radiation 202. In accordance with the present invention, a plurality of spatial patterns of transmitted electromagnetic radiation 208 is detected and stored by making use of a detector at a plurality of relative angular positions between the detector 204 and the cylindrically shaped medium 200. Each detected and recorded spatial pattern is indicative of the impurities located in the optical path of the radial components 208, 210, 212, 214 of radiation for a corresponding angular position. In other words the spatial pattern represents an image of the impurities on the diametral plane of the cylindrically shaped medium 200. In the illustrated setup, the medium 200 is stationary while the detector 204 is rotated counter clockwise around the rotation axis 206 to positions $\phi_i$, $\phi_{i+1}$, $\phi_{i+2}$, $\phi_{i+3}$. In these positions the detector 204 detects radiation 208, 210, 212, 214 emerging radially from the cylindrically shaped medium 200. The direction of this emerging radiation 208, 210, 212, 214 is perpendicular to the rotation axis 206 and perpendicular to the surface of the cylindrically shaped medium 200.

Since the detector 204 is elongated parallel to the rotation axis 206, in each of the positions $\phi_i$, $\phi_{i+1}$, $\phi_{i+2}$, $\phi_{i+3}$ the detector 204 detects radiation that is radially emerging from a corresponding diametral plane of the bulk medium 200. Impurities located in this diametral plane of the bulk medium interact with the irradiated radiation 202 and can thus be detected by the detector 204.

Figure 3:
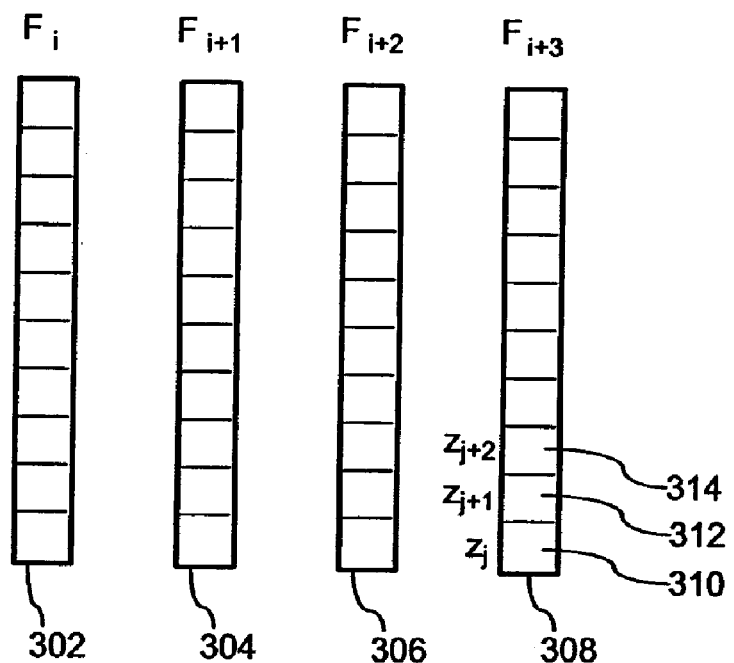
FIG. 3 is illustrative of arranging spatial patterns to generate the impurity diagram.
Figure 3:
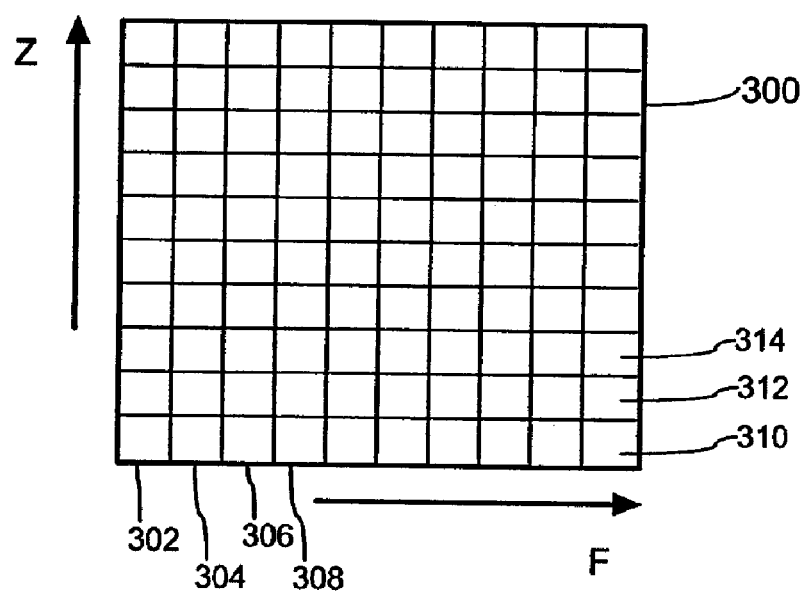

In accordance with the present invention, the plurality of spatial patterns that have been detected and stored for a plurality of relative angular positions between the detector and the cylindrically shaped medium are arranged in form of an impurity diagram. This impurity diagram is generated by plotting the spatial patterns against the relative angular positions. A spatial pattern referring to the angular position $\phi_i$ is arranged next to the spatial pattern recorded at an angular position $\phi_{i+1}$, where i is a running index for the multiplicity of different angular positions. For example, FIG. 3 shows an impurity diagram 300 consisting of spatial patterns 302, 304, 306, 308. The spatial pattern 302 represents the detected image at the relative angular position $\phi_i$, the spatial pattern 304 represents the recorded image corresponding to the relative angular position $\phi_{i+1}$, the spatial pattern 306 illustrates the image corresponding to the relative angular position $\phi_{i+2}$ and the spatial pattern 308 represents the image recorded at angular position $\phi_{i+3}$. Each of the spatial patterns 302, 304, 306, 308 has a number of pixels 310, 312, 314. The pixel 310 corresponds to the longitudinal position $z_j$, the pixel 312 corresponds to the longitudinal position $z_{j+1}$ and the pixel 314 corresponds to the longitudinal position $Z_{j+2}$.

The impurity diagram 300 is generated by arranging the spatial patterns 302, 304, 306, 308 side by side. In this way the impurity diagram 300 represents a plot of spatial patterns versus relative angular positions. The vertical dimension of the impurity diagram represents the longitudinal direction of the cylindrically shaped medium and the horizontal direction of the impurity diagram 300 represents the circumferential direction, hence the angle $\phi$ of a cylindrically shaped medium.

Since each spatial pattern 302, 304, 306 and 308 originates from a diametral plane of the cylindrically shaped medium, the impurity diagram consists of a series of images from a plurality of diametral planes for a plurality of various inspection angles $\phi_i$. According to a preferred embodiment of the invention, the impurity diagram can be analyzed in order to determine size and/or longitudinal position and/or the radial distance and/or the circumferential position of the impurities inside the bulk of the cylindrically shaped medium. An impurity located in the bulk of the cylindrically shaped medium generates an impurity trace in the impurity diagram 300. The impurity trace is indicative of the size, the longitudinal position, the radial distance and the circumferential position of the impurity within the bulk of the cylindrically shaped medium. Preferably, the radial components of the electromagnetic radiation and the detector are extended in the longitudinal direction of the cylindrically shaped medium. In this way the impurity diagram represents a two-dimensional plot in which the vertical direction represents the longitudinal direction of the cylindrically shaped medium and the horizontal direction represents the relative circumferential angular position.

The vertical position of the traces within the impurity diagram are indicative of the longitudinal position of the impurities within the bulk of the cylindrically shaped medium. The vertical expansion of the traces indicate the size of the impurities and the horizontal expansion of the traces within the impurity diagram are indicative of the radial distance of the impurities from the center of the circular cross section of the cylindrically shaped medium. Strictly speaking the vertical expansion of the traces in the impurity diagram is only indicative of the longitudinal expansion of the impurities in the bulk of the medium. In the case of gas bubbles embedded as impurities in the cylindrically shaped medium, and assumed that the impurities comprise a circular shape, the vertical expansion of the traces in the impurity diagram is also indicative of the diameter of the impurities in the bulk medium.

Figure 4:
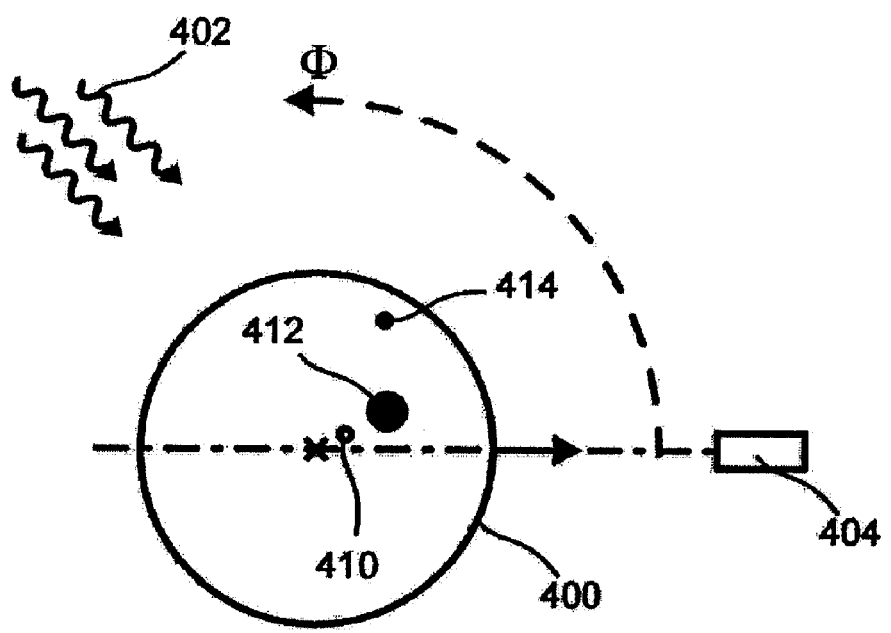
FIG. 4 shows a cylindrical cross section with impurities and the corresponding impurity diagram.
Figure 4:
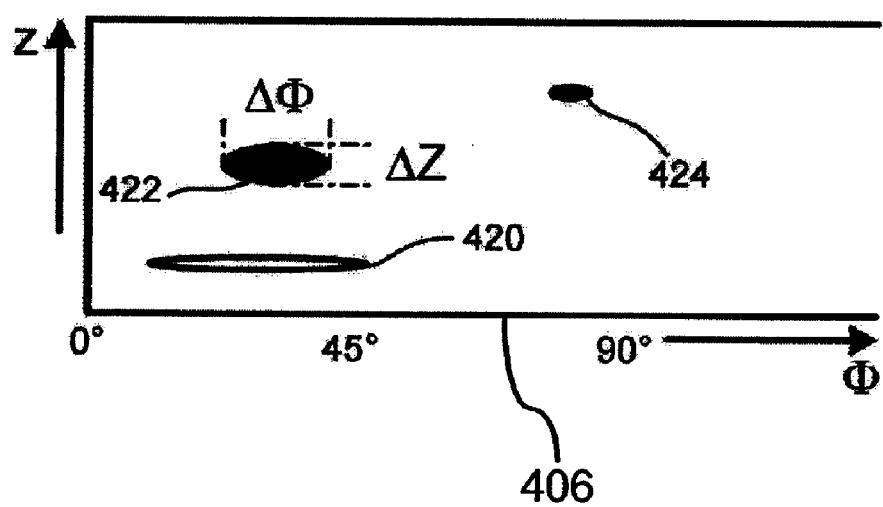

An analysis of the impurity diagram in accordance with the invention is illustrated by reference to FIG. 4. FIG. 4 shows a cross sectional view of the cylindrically shaped medium 400 with illumination 402 and detector 404. The medium 400 has impurities 410, 412 and 414. By rotating the detector 404 in positions $\phi$ and successively detecting spatial patterns from corresponding diametral planes, the impurity diagram 406 with impurity traces 420, 422 and 424 develops. The impurity trace 420 corresponds to the impurity 410, the impurity trace 422 corresponds to the impurity 412 and the impurity trace 424 corresponds to the impurity 414. From the vertical position z of the impurity traces 420, 422 and 424, the corresponding longitudinal positions of the impurities 410, 412 and 414 can be determined.

In case of spherical impurities the diameters and locations of the impurities can be determined exactly. The z-dimensions ΔZ of the impurity traces 420, 422 and 424 equal the diameters of the detected impurities 410, 412 and 414. From the angular widths, i.e. the horizontal dimensions of the impurity traces, the radial positions of the impurities can be determined. Given an angular width of the impurity trace of Δϕ, the radial distance R from the center of the cylindrical medium is given by $$R = \frac{\Delta Z}{2 \cdot \sin\left(\frac{\Delta \Phi}{2}\right)}.$$

Impurities being located in the center of the circular cross section of the cylindrically shaped medium 400, i.e. on the rotation axis, produce an impurity trace expanding over the entire angular axis of the impurity diagram 406. In this case other impurities located in the same cross section, i.e. the same z-position, are not detected. However, for typical densities of gas bubbles as impurities in a glass rod, this only occurs for less than 0.05% of all embedded gass bubbles.

Since the inspected diametral plane intersects the entire cylindrically shaped medium 400, the spatial pattern corresponding to an angle ϕ is identical to the spatial pattern corresponding to an angle ϕ+180°. This redundancy can be used to improve image quality and signal to noise ratio as well as to eliminate imaging errors. Thus, in accordance with the invention, the quality and the accuracy of the spatial patterns of the transmitted electromagnetic radiation can be improved by making use of a first and a second stored spatial pattern of electromagnetic radiation. The first spatial pattern corresponds to a first relative angular position and the second spatial pattern corresponds to a second relative angular position, the first and the second relative angular positions being shifted by 180 degrees. The spatial pattern originating from a relative angular position ϕ equals a spatial pattern originating from the relative angular position ϕ+180°. Making use of both redundant spatial patterns can improve the signal to noise ratio as well as eliminate imaging or inspection errors that are due to environmental conditions such as dust for example.

Figure 5:
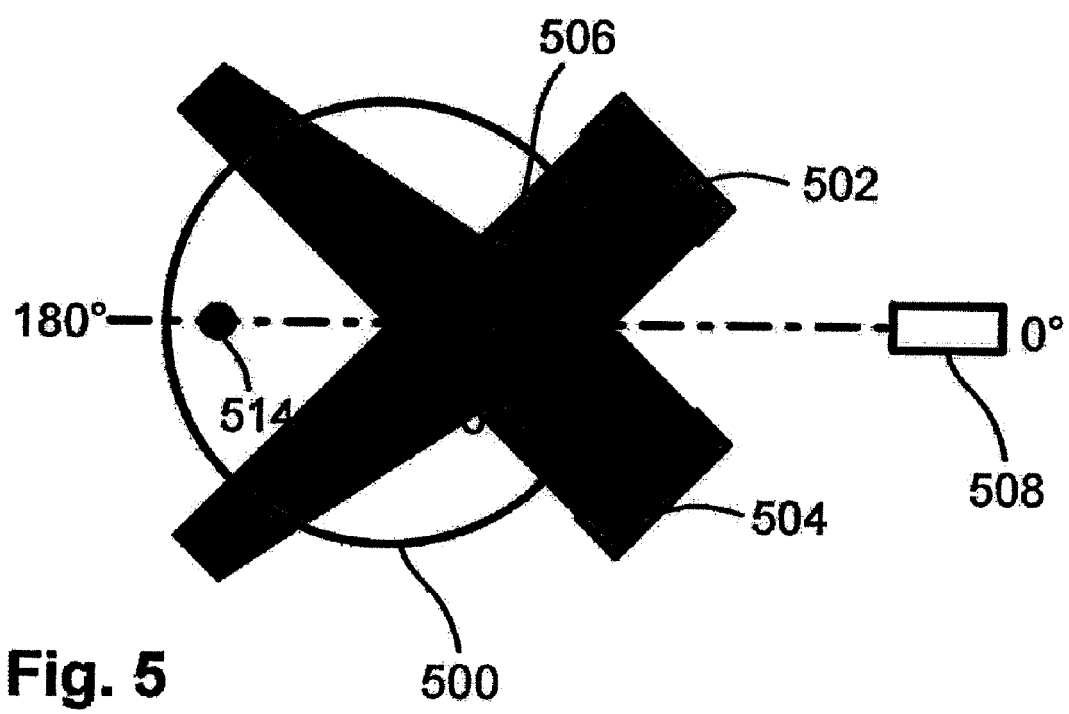
FIG. 5 shows an arrangement with two sources of electromagnetic radiation.

According to a further preferred embodiment of the invention, two or more sources of electromagnetic radiation generate an electromagnetic field distribution inside the cylindrically shaped medium in such a way, that the electromagnetic field distribution only covers the radius of the circular cross section of the cylindrically shaped medium. In this way not the entire diameter of the cylindrically shaped medium but only a portion of the diameter is exposed to electromagnetic radiation. FIG. 5 shows a cross sectional view of the cylindrically shaped medium 500 illuminated by two fields of electromagnetic radiation 502 and 504 in a way that the two radiation fields form an intersection area 506 and only illuminate a portion, e.g. one half, of the diameter of the cylindrically shaped medium. Electromagnetic radiation interacting with impurities in the diametral plane in this area 506 and emerging radially is detected by the detector 508. By means of the resulting impurity diagram, the circumferential position of the impurities 512, 514 can now be determined unequivocally. Whereas in the former case both impurities 512 and 514 would ambiguously be assigned either to the angle 0° or 180°. Here, only the impurity 512 is subject to exposure of electromagnetic radiation. In this configuration the detector 508 only detects impurity 512 which is then assigned to the relative angle of 0°. The impurity 514 can be detected correspondingly, when a relative angular movement of 180° between the detector and the cylindrically shaped medium has been performed. In this case the detector only detects radial components of electromagnetic radiation being scattered radially from impurities in the bulk of the medium. In this way the ambiguity whether an impurity is located at an angle ϕ of relative angular position or at an angle ϕ+180° is eliminated. Hence, the circumferential position of the impurities can be unequivocally determined.

According to a further preferred embodiment of the invention, at least a first and a second detector, being located at different circumferential positions with respect to the cylindrically shaped medium, are simultaneously used to detect and store radial components of electromagnetic radiation that is scattered by the impurities inside the bulk of the cylindrically shaped medium.

For example by making use of four detectors, being located at a circumferential angular separation of 90 degrees with respect to each other, the detectors and the cylindrically shaped medium only have to be relatively rotated by 90 degrees in order to detect and to record the images of all diametral planes of the cylindrically shaped medium. In this way the time needed to record a complete impurity diagram reduces by a factor of four compared to an arrangement that makes only use of one detector.

Alternatively, making use of a photographic film being arranged as a ring around the cylindrically shaped medium is also conceivable. For such an arrangement, a relative rotation between the cylindrically shaped medium and the detector is not needed. In this case, only the aperture has to rotate around the rotation axis of the cylindrically shaped medium, allowing only radial components of electromagnetic radiation to expose the photographic film.

According to a further preferred embodiment of the invention, the electromagnetic radiation and/or the detector have a first transverse expansion being parallel to the longitudinal axis of the cylindrically shaped medium and have a second transverse expansion perpendicular to the longitudinal axis of the cylindrically shaped medium and perpendicular to the radial component of the radiation. Preferably the first transverse expansion of the electromagnetic radiation and/or the detector is larger than the second transverse expansion of the electromagnetic radiation and/or the detector.

Furthermore, the first and the second expansion of the electromagnetic radiation do not significantly change during transmission through the cylindrically shaped medium. Due to the constant shape of the electromagnetic radiation during radial propagation through the cylindrically shaped medium, the size of the patterns, created by the impurities is independent of the radial position of the impurities in the bulk medium.

Since the detector preferably only receives the radial components of the electromagnetic radiation, in a preferred embodiment, the detector comprises a one-dimensional array of photo detectors or similar detection means. The longitudinal, first expansion of the photo detector limits the vertical size of the corresponding impurity diagram. The angular resolution of the impurity diagram is limited by different parameters, i.e. the second transverse expansion of the detector or the width of used apertures.

After one complete relative rotation between the detector and the cylindrically shaped medium, the impurity diagram displays a map of a volume of the cylindrically shaped medium given by the cross section multiplied by the first transverse expansion of the detector. After a complete rotation, i.e. the recording of the impurity diagram for $\phi 0 \ldots 360°$, the cylindrically shaped medium or the detector can be shifted in longitudinal direction and a subsequent impurity diagram can be recorded for a neighboring volume element of the cylindrically shaped medium.

According to a further preferred embodiment of the invention, the cylindrically shaped medium moves along its longitudinal direction with a longitudinal speed while the longitudinal position of a detector remains stationary. In this way cylindrically shaped media that move along the longitudinal direction can be subject to impurity inspection, which is often the case in industrial manufacturing processes of glass rods.

According to a further preferred embodiment of the invention, the electromagnetic radiation is irradiated in the axial direction through a cylindrically shaped medium. In this case the detector only detects and stores electromagnetic radiation that is scattered radially at the impurities inside the bulk of the cylindrically shaped medium and there is no need to rotate the radiation source with respect to the cylindrically shaped medium. Electromagnetic radiation is e.g. inherently present in the production process of glass rods due to the high temperature of the intermediate glass product evolving from the cast.

Figure 6:
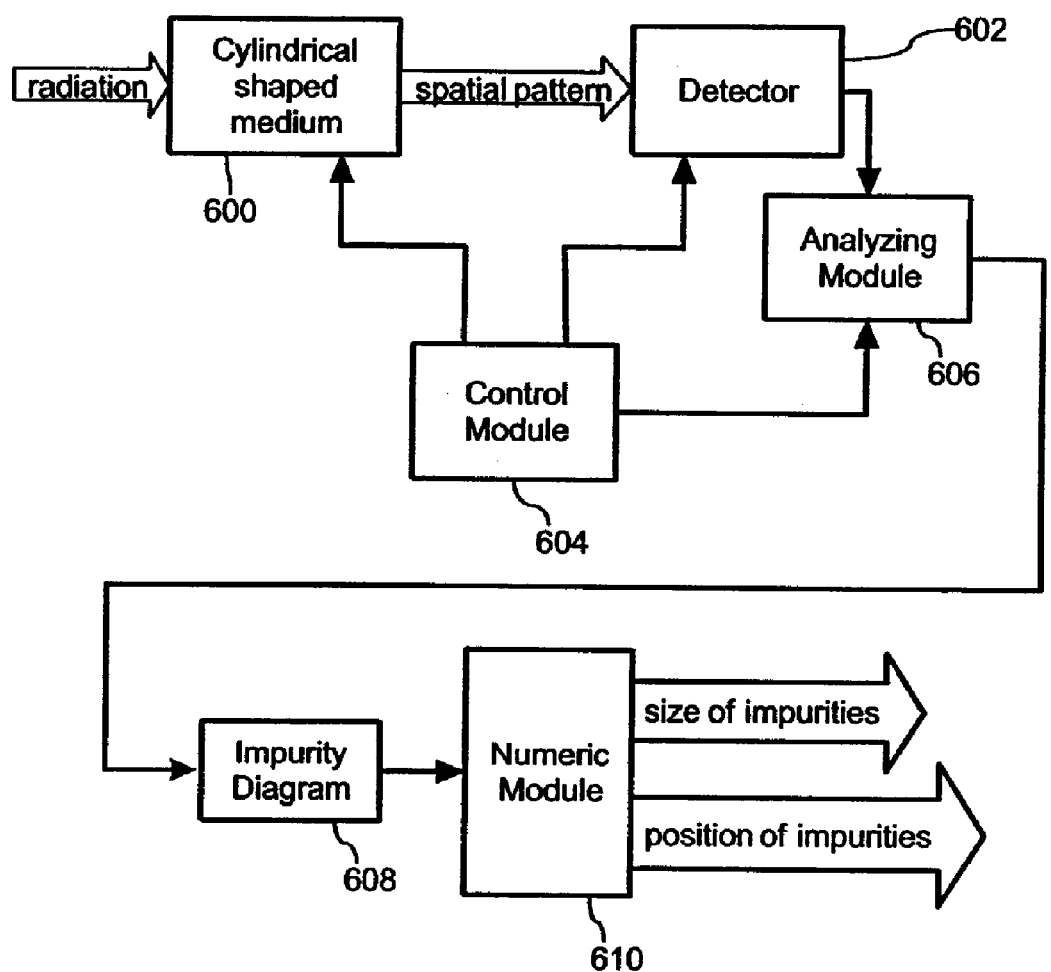
FIG. 6 shows a block diagram of the impurity detection system.

FIG. 6 is illustrative of a block diagram of the impurity detection system. The cylindrically shaped medium 600 is subject to electromagnetic radiation. After the electromagnetic radiation has interacted with the impurities in the medium 600, a corresponding spatial pattern is detected by a detector 602. The cylindrically shaped medium 600 and the detector 602 are controlled by means of a control module 604. The detector 602 generates an electrical or visual output that is sent to an analyzing module 606. The analyzing module 606 processes the signals obtained from the detector 602 and generates the impurity diagram 608. From the impurity diagram 608 impurity sizes and impurity positions are calculated by a numeric module 610.

The control module 604 controls the relative angular movement between the cylindrically shaped medium 600 and the detector 602. Furthermore the control module 604 transmits signals to the analyzing module 606. These signals being transferred from the control module 604 to the analyzing module 606 are indicative of a relative angular position between the detector 602 and the cylindrically shaped medium 600. In this way, the analyzing module 606 can assign the signals received from the detector 602 to the corresponding relative angular positions. Having the signals from the detector 602 representing the spatial patterns of the transmitted electromagnetic radiation and the assignment of these signals to the relative angular positions, the analyzing module 606 generates the impurity diagram 608.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of detecting impurities in a cylindrically shaped bulk transparent medium having an axis along a longitudinal direction, the method comprising the steps of:

illuminating the cylindrically shaped bulk transparent medium with electromagnetic radiation, the radiation having radiation components emerging radially from the medium;

receiving at least some of the radiation components by a detector for detecting impurities of the medium;

storing a plurality of spatial patterns of the radiation components for a plurality of relative angular positions between the detector and the cylindrically shaped bulk medium, the spatial patterns being indicative of the impurities of the medium;

forming an impurity diagram comprising an arrangement of the spatial patterns arranged in accordance with the plurality of relative angular positions;

analyzing said impurity diagram to identify an impurity; and determining from said impurity diagram for said identified impurity an angular width $\Delta\phi$ and a longitundinal width $\Delta Z$.

2. The method of claim 1 further comprising determining a radial position, R of said identified impurity from said axis of said cylindrically shaped bulk medium according to the formula $$R = \frac{\Delta Z}{2 \cdot \sin\left(\frac{\Delta\Phi}{2}\right)}.$$

3. The method according to claim 1 further comprising improving the quality and the accuracy of the spatial pattern of detected radiation by detecting a first and a second radiation pattern at a first and a second relative angular position, the first and the second relative angular positions being shifted by 180 degrees.

4. The method according to claim 1, wherein two or more sources of electromagnetic radiation generate an electromagnetic field distribution inside the cylindrically shaped medium, the electromagnetic field distribution covering a portion of the circular cross section of the cylindrically shaped medium.

5. The method according to claim 1, wherein the cylindrically shaped medium and the detector move in a translational way relative to each other along the longitudinal direction of the cylindrically shaped medium with a longitudinal speed.

6. The method according to claim 1, wherein the cylindrically shaped medium is illuminated in axial direction and the detector detects electromagnetic radiation being scattered radially at the impurities inside the medium.

7. The method according to claim 1, wherein at least a first and a second detector detect electromagnetic radiation being scattered radially at the impurities inside the medium.

8. A system for detecting impurities in a cylindrically shaped transparent bulk medium having an axis along a longitudinal direction, the system comprising:

a radiation source for illuminating the cylindrically shaped transparent bulk medium with electromagnetic radiation;

a detector for receiving radial components of radiation that emerge radially from the medium;

means for storing a plurality of spatial patterns of the radial components for a plurality of relative angular positions between the detector and the cylindrically shaped medium, the plurality of spatial patterns being indicative of the impurities of the medium;

means for analyzing said plurality of spatial patterns to identify an impurity; and means for determining an angular width Δϕ and a longitundinal width ΔZ of said identified impurity along said longitudinal direction from said plurality of spatial patterns.

9. The system according to claim 8, farther comprising:

means for determining a radial position R of said identified impurity from said axis of said cylindrically shaped bulk medium according to the formula $$R = \frac{\Delta Z}{2\sin\left(\frac{\Delta \phi}{2}\right)}.$$

10. The system according to claim 8, further comprising means for performing a relative angular movement of the cylindrically shaped medium and the detector around said axis of the cylindrically shaped bulk medium.

11. The system according to claim 10 further comprising a control module for controlling the relative angular movement between the cylindrically shaped bulk medium and the detector.

12. The system according to claim 8 further comprising a plurality of radiation detectors for detecting radial components, said plurality of radiation detectors arranged at relative angular positions around said axis of the cylindrically shaped bulk medium.

13. The system according to claim 8 further comprising means for forming an impurity diagram comprising an arrangement of the plurality of spatial patterns arranged in accordance with the plurality of relative angular positions.

14. The system according to claim 8, wherein the detector has a first transverse expansion parallel to the longitudinal axis of the cylindrically shaped medium and a second transverse expansion perpendicular to said axis of the cylindrically shaped bulk medium, the first transverse expansion of the detector being larger than the second transverse expansion of the detector.

15. The system according to claim 8, further comprising two or more sources of electromagnetic radiation generating an electromagnetic field distribution inside the cylindrically shaped bulk medium, the electromagnetic field distribution covering a portion of the circular cross section of the cylindrically shaped bulk medium.

16. The system according to claim 15, further comprising:

means for storing a plurality of spatial patterns of the radial components of the electromagnetic field distribution for a plurality of relative angular positions between the detector and the cylindrically shaped bulk medium, the plurality of spatial patterns being indicative of the impurities of the bulk medium; and means for determining the circumferential position of said identified impurity in accordance with the plurality of spatial patterns.

17. The system according to claim 8, further comprising means for moving the cylindrically shaped bulk medium and the detector in a translational way relative to each other along the longitudinal direction of the cylindrically shaped medium with a longitudinal speed.

18. The system according to claim 12 wherein at least first and second detectors of said plurality of radiation detectors are arranged at a relative angular position of 180° from each other around said axis of the cylindrically shaped bulk medium.

* * * * *